(12) United States Patent
Kojima

(10) Patent No.: US 10,462,440 B2
(45) Date of Patent: Oct. 29, 2019

(54) IMAGE PROCESSING APPARATUS

(71) Applicant: OLYMPUS CORPORATION, Tokyo (JP)

(72) Inventor: Koji Kojima, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/154,931

(22) Filed: Oct. 9, 2018

(65) Prior Publication Data

US 2019/0052854 A1 Feb. 14, 2019

Related U.S. Application Data

(63) Continuation of application No. PCT/JP2017/014542, filed on Apr. 7, 2017.

(30) Foreign Application Priority Data

Apr. 19, 2016 (JP) ................. 2016-083603

(51) Int. Cl.
| | |
|---|---|
| *H04N 9/73* | (2006.01) |
| *H04N 5/232* | (2006.01) |
| *H04N 5/262* | (2006.01) |
| *G02B 23/24* | (2006.01) |
| *H04N 5/225* | (2006.01) |
| *A61B 1/00* | (2006.01) |

(52) U.S. Cl.
CPC .......... *H04N 9/73* (2013.01); *A61B 1/00009* (2013.01); *G02B 23/24* (2013.01);
(Continued)

(58) Field of Classification Search
CPC ............ A61B 1/00009; A61B 1/00039; G02B 23/24; H04N 2005/2255; H04N 5/23245;
(Continued)

(56) References Cited

U.S. PATENT DOCUMENTS

| | | | |
|---|---|---|---|
| 5,111,804 A | 5/1992 | Funakoshi | |
| 2006/0038894 A1* | 2/2006 | Chan ...................... | H04N 5/232 348/222.1 |
| 2006/0238623 A1* | 10/2006 | Ogawa ................. | H04N 1/2112 348/220.1 |
| 2008/0043108 A1* | 2/2008 | Jung ...................... | H04N 5/232 348/207.1 |

(Continued)

FOREIGN PATENT DOCUMENTS

| | | |
|---|---|---|
| JP | H02-213817 A | 8/1990 |
| JP | 2000-139833 A | 5/2000 |

(Continued)

OTHER PUBLICATIONS

International Search Report dated Jun. 20, 2017 issued in International Application No. PCT/JP2017/014542.

*Primary Examiner* — Chiawei Chen
(74) *Attorney, Agent, or Firm* — Scully, Scott, Murphy & Presser, P.C.

(57) ABSTRACT

An image processing apparatus determines, with a freeze signal, an image of a freeze target, or determines, with no freeze signal, a latest image as an image to be displayed; performs color-balance adjustments using first and second parameters, based on the imaging signal of the determined image, thereby generating first and second imaging signals, respectively; generates a display purpose imaging signal, based on the generated first imaging signal; detects signals of plural color components included in the second imaging signal; calculates, based on the detected signals, a color-balance parameter for the color-balance adjustment; sets, when inputting no freeze signal, a latest color-balance parameter calculated, as the first and the second parameters, or sets, when the freeze instruction signal is input, a color-balance parameter corresponding to the image of the freeze target as the first parameter and the latest color-balance parameter as the second parameter.

5 Claims, 7 Drawing Sheets

(52) U.S. Cl.
CPC ....... *H04N 5/23245* (2013.01); *H04N 5/2627* (2013.01); *H04N 9/735* (2013.01); *A61B 1/00039* (2013.01); *H04N 2005/2255* (2013.01)

(58) Field of Classification Search
CPC ........ H04N 5/2627; H04N 9/73; H04N 9/735; H04N 1/60; H04N 1/6077; H04N 1/608; H04N 13/133; H04N 1/212; H04N 5/343; G09G 2320/0666
See application file for complete search history.

(56) References Cited

U.S. PATENT DOCUMENTS

| | | | | |
|---|---|---|---|---|
| 2010/0208098 A1* | 8/2010 | Ogawa | ............... | H04N 5/23245 348/223.1 |
| 2012/0026379 A1* | 2/2012 | Mori | ....................... | G03B 17/20 348/333.02 |
| 2012/0140985 A1* | 6/2012 | Hattori | ................... | H04N 5/147 382/103 |
| 2014/0267812 A1* | 9/2014 | Kennedy | ................ | A61B 1/045 348/211.3 |
| 2017/0013243 A1* | 1/2017 | Fujiwara | ................ | H04N 9/735 |

FOREIGN PATENT DOCUMENTS

| | | |
|---|---|---|
| JP | 2005-319213 A | 11/2005 |
| WO | 2011/155429 A1 | 12/2011 |

\* cited by examiner

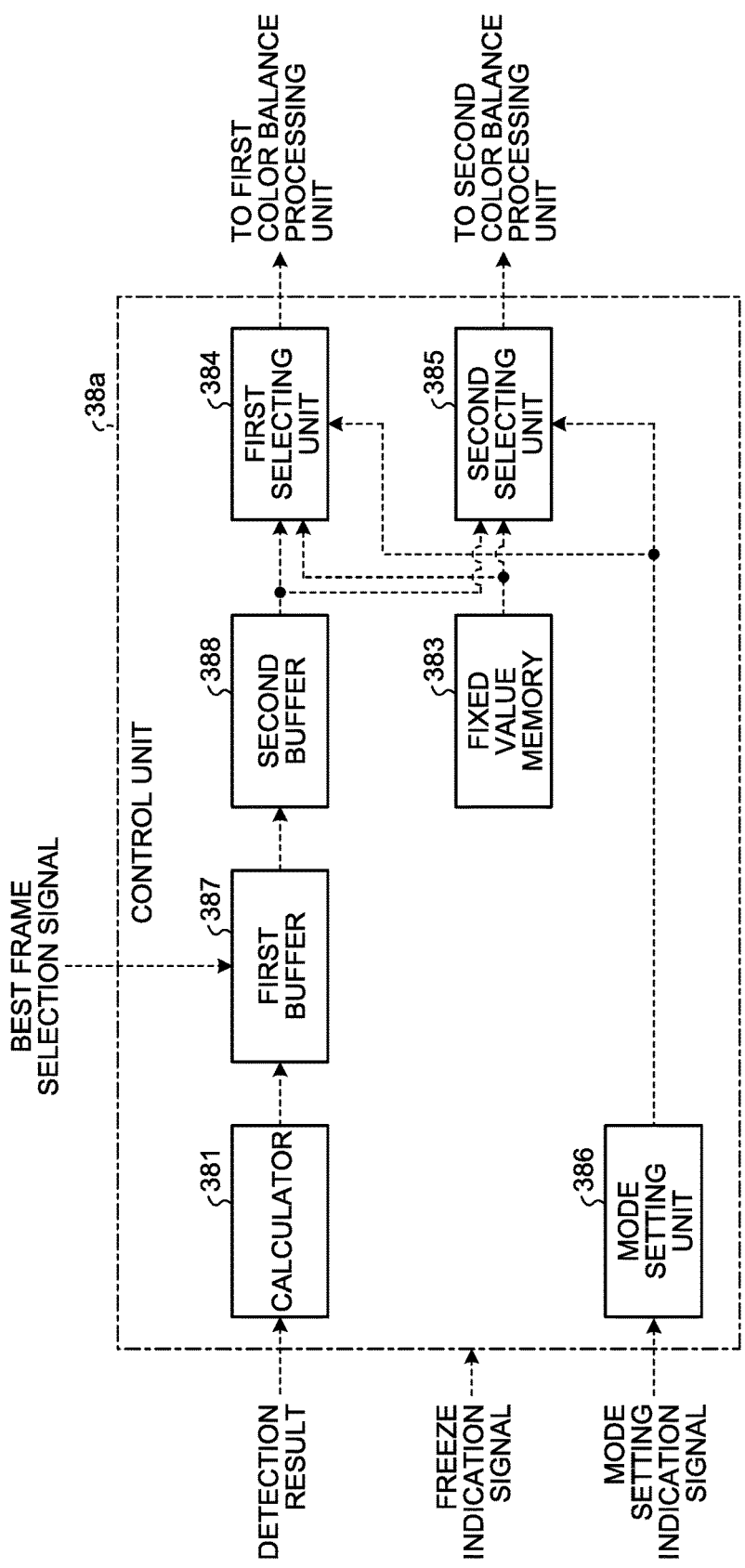

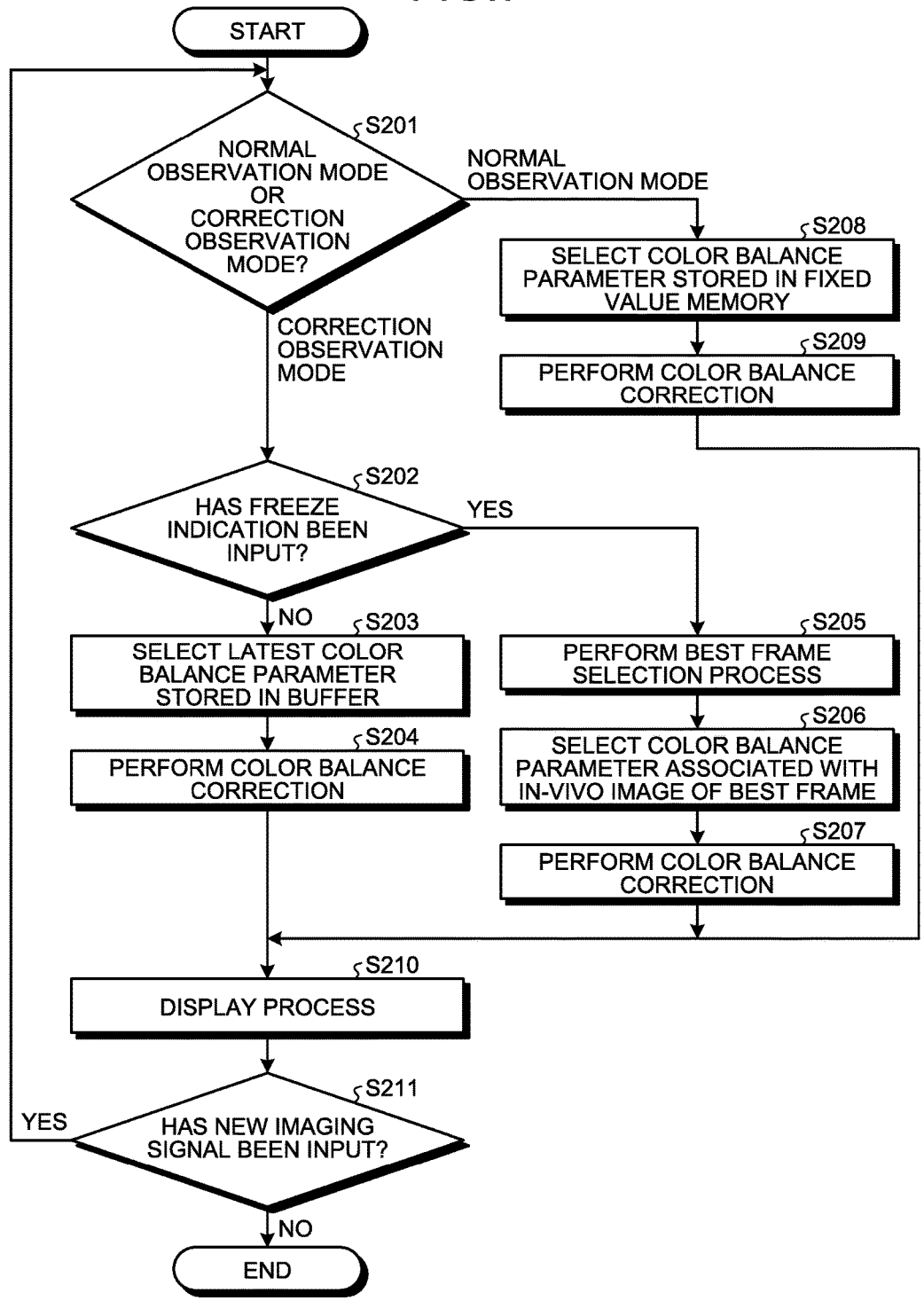

IMAGE PROCESSING APPARATUS

CROSS-REFERENCE TO RELATED APPLICATION

This application is a continuation of PCT International Application No. PCT/JP2017/014542 filed on Apr. 7, 2017 which claims the benefit of priority from Japanese Patent Application No. 2016-083603, filed on Apr. 19, 2016, the entire contents of which are incorporated herein by reference.

BACKGROUND

The present disclosure relates to an image processing apparatus.

In the past, in the medical field, an endoscope system has been used when organs of subjects, such as patients, are observed. The endoscope system includes an endoscope having an insertion portion that is introduced into a subject, that has an image sensor provided at, for example, a distal end, and that has a flexible narrow tip; a processing device that is connected to the proximal end side of the insertion portion via a cable, that performs image processing on an in-vivo image in accordance with an imaging signal captured by the image sensor, and that allows an in-vivo image to be displayed on a display unit or the like; and a light source device that emits illumination light for illuminating inside the subject.

When an in-vivo image is acquired by using the endoscope system, after having inserted the endoscope into the subject, the illumination light, such as white light or special light formed of light in a predetermined wavelength band, is emitted from the distal end of the endoscope toward a biological tissue inside the subject, and the image sensor captures the in-vivo image. The processing device displays, on a display unit, the in-vivo image that is based on an imaging signal of the image captured by the image sensor. A user, such as a doctor, observes inside the subject based on the in-vivo image displayed on the display unit. As the technology used to observe a subject, there is a known technology that can sequentially display the in-vivo image obtained by an endoscope as a moving image, and the display the in-vivo image as a still image when a freeze command is executed (for example, see International Publication Pamphlet No. WO 2011/155429). The technology disclosed in International Publication Pamphlet No. WO 2011/155429 has a memory that stores therein a plurality of in-vivo images. When an input of a freeze command is received, an in-vivo image with small blurring is selected from a plurality of in-vivo images stored in the memory; and the selected in-vivo image is displayed as a still image.

SUMMARY

The present disclosure has been made in view of the above, and is directed to an image processing apparatus.

According to an aspect of the present disclosure, an image processing apparatus is provided. The image processing apparatus includes a processor comprising hardware, wherein the processor is configured to: acquire, in time series, an imaging signal generated by capturing an object; determine, when a freeze instruction signal that allows an image based on the imaging signal to be displayed as a still image is input, an image of a freeze target, thereby to specify an imaging signal corresponding to the image of the freeze target, or determine, when the freeze instruction signal is not input, a latest image as an image to be displayed, thereby to specify an imaging signal corresponding to the image to be displayed; perform a color balance adjustment process by using a first color balance parameter, based on the imaging signal corresponding to the image which is determined to be either one of the image of the freeze target and the latest image in the determining, thereby to generate a first imaging signal; generate a display purpose imaging signal, based on the generated first imaging signal; perform the color balance adjustment process by using a second color balance parameter, based on the imaging signal corresponding to the image which is determined to be either one of the image of the freeze target and the latest image in the determining, in parallel with the performing the color balance adjustment process by using the first color balance parameter, thereby to generate a second imaging signal; detect signals of a plurality of color components that are included in the second imaging signal; calculate, based on the detected signals, a color balance parameter used for performing the color balance adjustment process; and set, when the freeze instruction signal is not input, a latest color balance parameter that has been calculated in the calculating as the first and the second color balance parameters, or set, when the freeze instruction signal is input, a color balance parameter corresponding to the image of the freeze target as the first color balance parameter and the latest color balance parameter as the second color balance parameter.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a block diagram of a relevant part of the endoscope system according to the second embodiment of the present disclosure; and FIG. 7 is a flowchart illustrating image processing performed by the endoscope system according to the second embodiment of the present disclosure.

DETAILED DESCRIPTION

In the following, modes for carrying out the present disclosure (hereinafter, referred to as an "embodiment") will be described. In the embodiment, as an example of a system that includes an image processing apparatus according to the present disclosure, an endoscope system for medical use that captures images inside a subject, such as a patient, and that displays the images will be described. Furthermore, the present disclosure is not limited to the following embodi-

First Embodiment

Figure 1:
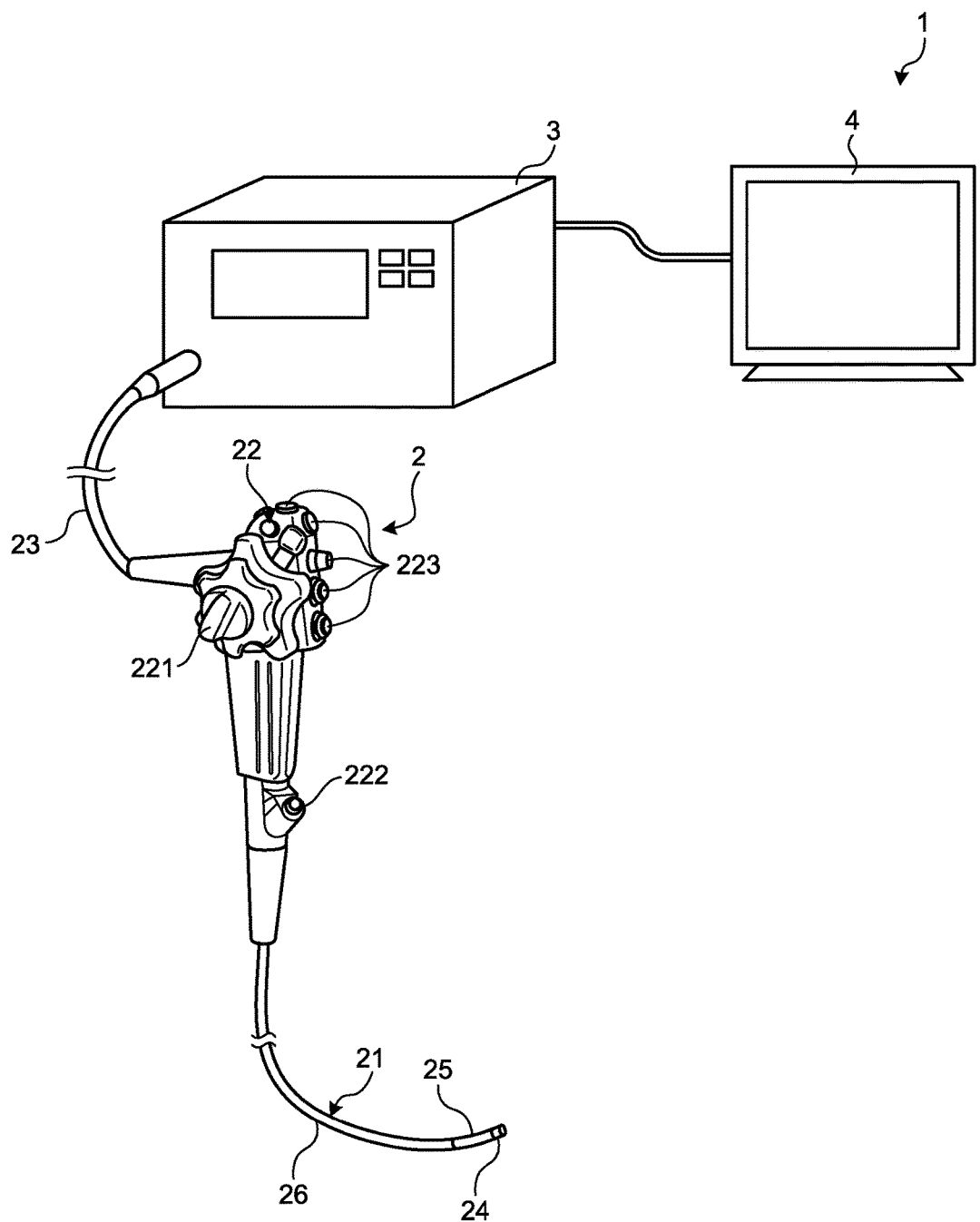
FIG. 1 is a diagram schematically illustrating, an endoscope system according to a first embodiment of the present disclosure.
Figure 2:
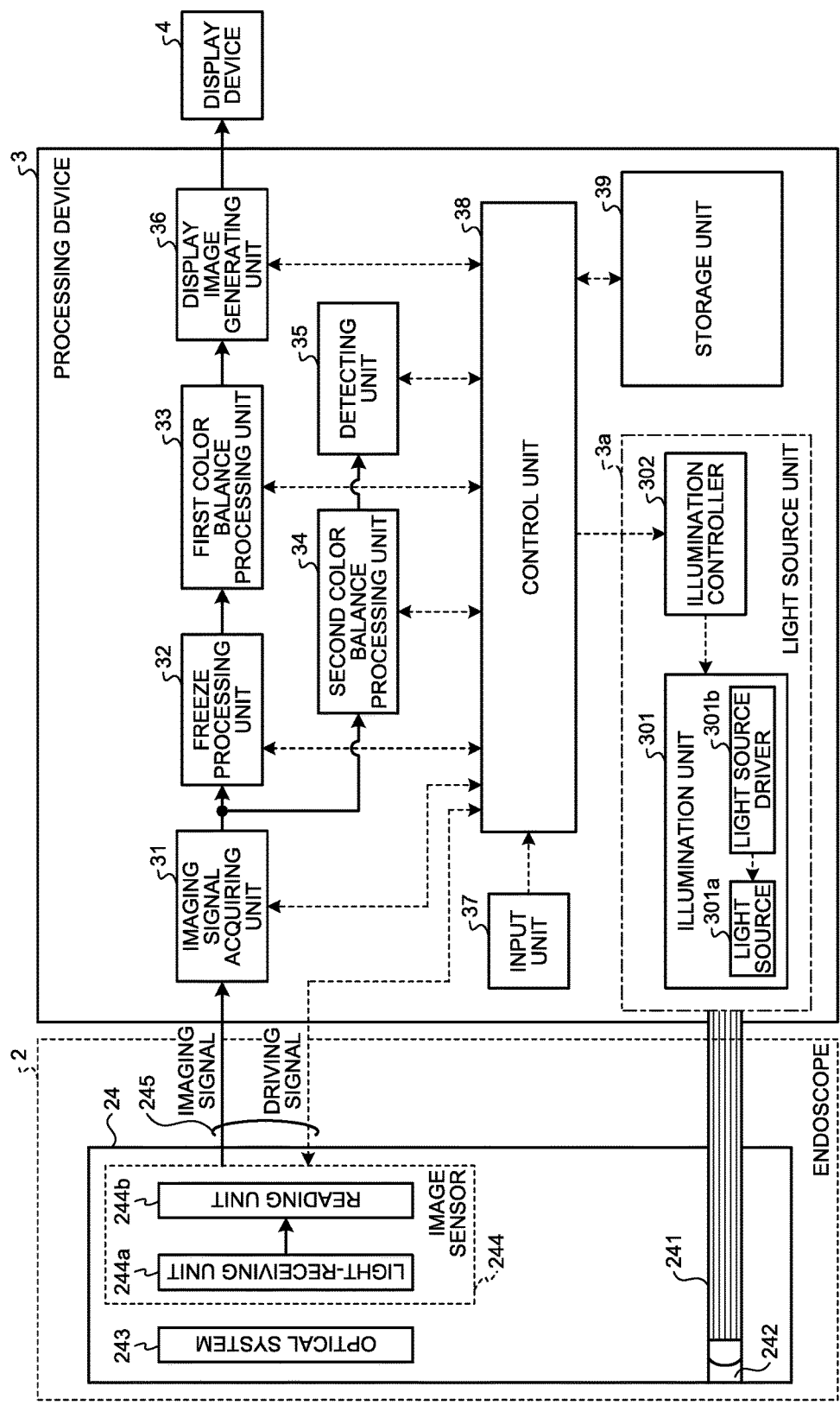
FIG. 2 is a block diagram of the endoscope system according to the first embodiment of the present disclosure.

FIG. 1 is a diagram schematically illustrating an endoscope system according to a first embodiment of the present disclosure. FIG. 2 is a block diagram of the endoscope system according to the first embodiment of the present disclosure. Furthermore, in FIG. 2, arrows with solid lines indicate a flow of an electrical signal related to an image and arrows with broken lines indicate a flow of control signals.

An endoscope system 1 illustrated in FIG. 1 and FIG. 2 includes an endoscope 2 that has a distal end portion inserted inside the subject and that captures an in-vivo image of a subject; a processing device 3 that includes a light source unit 3a that produces illumination light to be emitted from the distal end of the endoscope 2, that performs predetermined signal processing on the imaging signal captured by the endoscope 2, and that performs overall control of the endoscope system 1; and a display device 4 that displays an in-vivo image generated from the signal processing performed by the processing device 3.

The endoscope 2 includes an insertion portion 21 having a flexible narrow tip shape; an operating unit 22 that is connected to the proximal end side of the insertion portion 21 and that receives an input of various operation signals; and a universal cord 23 that extends from the operating unit 22 in the direction different from the direction in which the insertion portion 21 extends and that has various built-in cables connected to the processing device 3 (including the light source unit 3a). In the first embodiment, a description will be given with the assumption that the insertion portion 21 is inserted into the urinary bladder of a subject and captures an in-vivo image of the urinary bladder. When observing an interior of the urinary bladder, Narrow Band Imaging (NBI) observation is performed that uses narrow-band light as special light in this embodiment, while observation may be performed by using white light in other embodiments.

The insertion portion 21 includes a distal end portion 24 that has a built-in image sensor 244 in which pixels that generate signals by receiving light and performing photoelectric conversion are arrayed in a two-dimensional state; a bending portion 25 that is formed so as to be capable of being freely bent by a plurality of bending sections; and a flexible tube portion 26 having a flexible elongated shape connected to the proximal end side of the bending portion 25. The insertion portion 21 is inserted into the body cavity of the subject and the image sensor 244 captures an object, such as a biological tissue, located at the position in which external light does not reach.

The distal end portion 24 is formed by using glass fibers or the like and includes a light guide 241 that forms a light guide path of the light emitted by the light source unit 3a; an illumination lens 242 provided at the distal end of the light guide 241; an optical system 243 used for condensing light; and an image sensor 244 (imaging unit) that is provided at an imaging position of the optical system 243, that receives light condensed by the optical system 243, that performs photoelectric conversion by converting the light to an electrical signal, and that performs predetermined signal processing.

The optical system 243 is formed by using one or more lenses, and has an optical zoom mechanism, which changes the angle of view, and a focus function, which changes a focal point.

The image sensor 244 performs photoelectric conversion on the light received from the optical system 243 and generates an electrical signal (imaging signal). Specifically, the image sensor 244 includes a light-receiving unit 244a in which a plurality of pixels each of which includes a photodiode that accumulates electric charges in accordance with an amount of light and a condenser that converts the electric charges transferred from the photodiode to a voltage level is arrayed in a matrix form and each of the pixels performs photoelectric conversion on the light from the optical system 243 and generates an electrical signal. The image sensor 244 also includes a reading unit 244b. The reading unit 244b sequentially reads the electrical signals generated by the pixels that have been arbitrarily set as reading targets from the plurality of pixels included in the light-receiving unit 244a, and outputs the electrical signals as an imaging signal. In the light-receiving unit 244a, a color filter is provided and each of the pixels receives light with one of the wavelength bands among the wavelength bands of the color components of red (R), green (G), and blue (B). The image sensor 244 controls various operations of the distal end portion 24 in accordance with the driving signal received from the processing device 3. The image sensor 244 is implemented by using, for example, a charge coupled device (CCD) image sensor or a complementary metal oxide semiconductor (CMOS) image sensor. Furthermore, the image sensor 244 may be a single-panel image sensor or may also be, for example, a three-panel type image sensor using a plurality of image sensors.

The operating unit 22 (FIG. 1) includes a bending knob 221 that allows the bending portion 25 to be bent in the vertical direction and in the horizontal direction; a treatment instrument insertion portion 222 that allows a treatment instrument, such as biopsy forceps, an electric scalpel, or an examination probe, to be inserted into the body cavity of the subject; and a plurality of switches 223 that are an operation input unit used to input an operation instruction signal of, in addition to the processing device 3, a peripheral device, such as an air supply unit, a water supply unit, a screen display controller. The treatment instrument inserted from the treatment instrument insertion portion 222 is output from an opening (not illustrated) via a treatment instrument channel (not illustrated) provided at the distal end portion 24.

The universal cord 23 includes at least the light guide 241, and an assembled cable 245 formed by assembling one or a plurality of signal lines. The assembled cable 245 includes a signal line that is used to transmit an imaging signal, another signal line that is used to transmit a driving signal for driving the image sensor 244, and a yet another signal line that is used to transmit information including specific information related to the endoscope 2 (the image sensor 244). In this embodiment, electrical signals are transmitted through the signal lines, or the assembled cable 241. However, in other embodiments, optical signals, instead of the electrical signals, may be transmitted through an optical fiber between the endoscope 2 and the processing device 3. Alternatively, radio signals, instead of the electrical signals or the optical signals, may be transmitted between the endoscope 2 and the processing device 3 by employing wireless communication.

In the following, the processing device 3 will be described. The processing device 3 includes an imaging signal acquiring unit 31, a freeze processing unit 32, a first color balance processing unit 33, a second color balance processing unit 34, a detecting unit 35, a display image generating unit 36, an input unit 37, a control unit 38, and a storage unit 39. Furthermore, the image processing apparatus according to the present embodiment is formed by using at least the first color balance processing unit 33, the second color balance processing unit 34, the detecting unit 35, the display image generating unit 36, and the control unit 38.

The imaging signal acquiring unit 31 receives, from the endoscope 2, an imaging signal that is captured by the image sensor 244 and that includes image data used for creating an in-vivo image. The imaging signal acquiring unit 31 performs signal processing, such as noise removal, A/D conversion, and synchronization process (for example, performed when an imaging signal for each color component is obtained by using a color filter or the like), on the acquired imaging signal. The imaging signal acquiring unit 31 generates a process signal (processed imaging signal) including the in-vivo image to which the RGB color components have been added by the signal processing described above. The imaging signal acquiring unit 31 outputs the generated process signal to the freeze processing unit 32 and the second color balance processing unit 34. The imaging signal acquiring unit 31 is formed by using a general purpose processor, such as a central processing unit (CPU), or a special purpose processor, such as various arithmetic circuits or the like including an application specific integrated circuit (ASIC).

If the input unit 37 receives an input of a freeze instruction signal, the freeze processing unit 32 determines the in-vivo image corresponding to the process signal input from the imaging signal acquiring unit 31 should be displayed on the display device 4 as a freeze image. The freeze processing unit 32 inputs, to the first color balance processing unit 33, the process signal correspond to the in-vivo image that has been determined as the freeze image to be displayed on the display device 4. Furthermore, if an input of freeze instruction signal is not received, the freeze processing unit 32 sequentially outputs the process signals that have been input from the imaging signal acquiring unit 31 to the first color balance processing unit 33. Furthermore, if the freeze processing unit 32 determines the in-vivo image to be displayed as the freeze image, during a still image display period due to the operation of the freeze process, the freeze processing unit 32 does not receive a process signal input from the imaging signal acquiring unit 31, or discards the process signal and does not output the process signal to the first color balance processing unit 33, even when receiving the process signal. After the freeze process has been released, the freeze processing unit 32 outputs, to the first color balance processing unit 33, the process signal that is newly input from the imaging signal acquiring unit 31 as the in-vivo image of a display purpose moving image. Thus, the in-vivo images displayed on the display device 4 after the freeze process are the in-vivo images except for the in-vivo images that supposed to be obtained during the still image display period, i.e., the in-vivo images with large intervals in terms of time series with respect to the in-vivo images displayed immediately before the freeze process. Consequently, in the in-vivo images displayed before and after the freeze process, a change in the object image sometimes becomes great when compared with a case in which the in-vivo images adjacent to each other in time series are displayed as a moving image. The freeze processing unit 32 is formed of a CPU, an ASIC, or the like.

Based on the color balance parameters that are input from the control unit 38, the first color balance processing unit 33 performs a color balance adjustment process on the process signals that are input from the freeze processing unit 32. Specifically, the first color balance processing unit 33 adjusts the signal level of the process signal to be input to each of the red (R), green (G), and blue (B) channels. The first color balance processing unit 33 outputs the image signals generated by the color balance adjustment process to the display image generating unit 36. The first color balance processing unit 33 is formed of a CPU, an ASIC, or the like.

Based on the color balance parameters input from the control unit 38, the second color balance processing unit 34 performs color balance adjustment process on the process signals that are input from the imaging signal acquiring unit 31. Specifically, based on the color balance input from the control unit 38, the second color balance processing unit 34 adjusts the signal level of the process signal of each of the red (R), green (G), and blue (B) channel color components. The second color balance processing unit 34 outputs the image signals generated by the color balance adjustment process to the detecting unit 35. The second color balance processing unit 34 is formed of a CPU, an ASIC, or the like.

The detecting unit 35 detects a signal value (luminance value of each pixel) from the Y signal of the luminance component, the R signal of the red component, the G signal of the green component, and the B signal of the blue component that are included in the image signal input from the second color balance processing unit 34 and then sets the signal value of each of the components to the detection value. The detecting unit 35 outputs the generated detection value to the control unit 38. Furthermore, the detecting unit 35 may also output the average value of the luminance values as the detection value or may also output the maximum value, the minimum value, or the like as the detection value. The detecting unit 35 is formed of a CPU, an ASIC, or the like.

The display image generating unit 36 performs the signal processing on the image signals generated by the first color balance processing unit 33 such that the image signals become signals displayable on the display device 4, and then generates display purpose image signals. Specifically, the display image generating unit 36 generates the display purpose image signals by performing an enhancement process, a compression process, or the like on the image signals. If the input signals are classified into each of the RGB color components, the display image generating unit 36 performs an interpolation process on each of the input color components and generates the image signals to which the RGB color component is added to each of the pixel positions. The display image generating unit 36 sends the generated display purpose image signals to the display device 4. The display image generating unit 36 is formed of a CPU, an ASIC, or the like.

Furthermore, if the in-vivo image associated with the image signal input from the first color balance processing unit 33 is the in-vivo image of the freeze target, the display image generating unit 36 displays the in-vivo image of the freeze target on the display device 4 as a still image during the previously set period, for example, during the period for which several frames of in-vivo images are displayed.

The input unit 37 is implemented by using a keyboard, a mouse, a switch, or a touch panel and receives an input of various signals, such as operation instruction signals, that indicate the operation of the endoscope system 1. Furthermore, the input unit 37 may also include a switch provided in the operating unit 22 or include a portable terminal, such as an external tablet computer.

The control unit 38 is formed of a CPU, an ASIC, a memory, or the like; controls each component including the image sensor 244 and the light source unit 3a; and performs input/output control of information with respect to each component. The control unit 38 refers to the control information data (for example, read out timing, etc.) that is used to perform imaging control and that is stored in the storage unit 39 and then sends the control information data as the driving signal to the image sensor 244 via a predetermined signal line that is included in the assembled cable 245.

Furthermore, based on the detection result obtained by the detecting unit 35 and the instruction signal received by the input unit 37, the control unit 38 performs input control of the color balance parameters that are input to the first color balance processing unit 33 and the second color balance processing unit 34.

Figure 3:
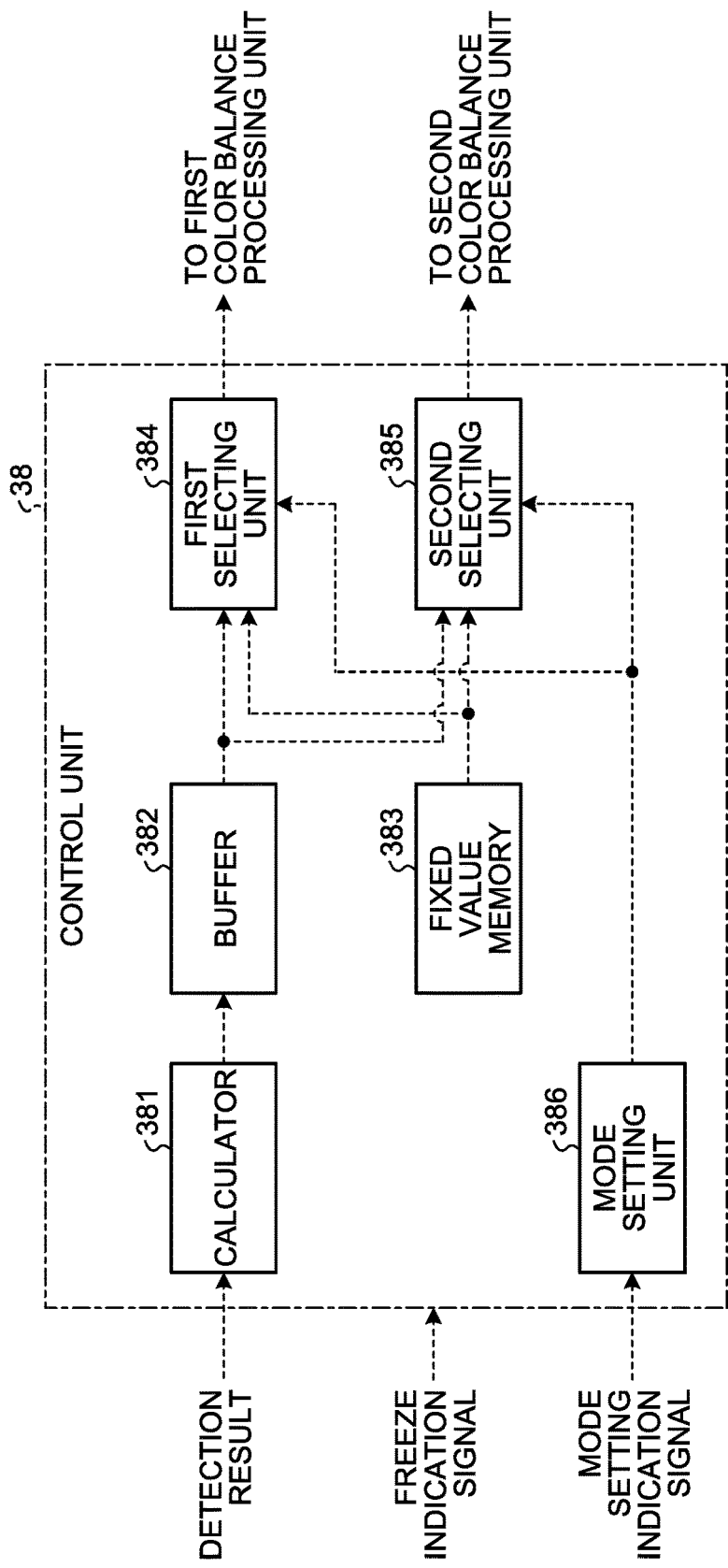
FIG. 3 is a block diagram of a relevant part of the endoscope system according to the first embodiment of the present disclosure.

FIG. 3 is a block diagram of a relevant part of the endoscope system according to the first embodiment of the present disclosure, specifically the block diagram of the control unit 38. The control unit 38 includes a calculator 381, a buffer 382, a fixed value memory 383, a first selecting unit 384, a second selecting unit 385, and a mode setting unit 386. A parameter selecting unit is formed of the first selecting unit 384 and the second selecting unit 385.

The calculator 381 calculates a color balance parameter based on the detection value that is input from the detecting unit 35. Specifically, the calculator 381 calculates DB/DG, where the detection value of the G component is DG and the detection value of the B component is DB. Here, when performing NBI observation, yellow is displayed as a false color of red. There may be a case in which urine is included in the urinary bladder, if blue light is absorbed by urine, the portion that is normally yellow is displayed in reddish color. The calculator 381 compensates blue light absorption due to urine and calculates DB/DG described above as the color balance parameter for correcting the color of the yellow portion. The calculator 381 outputs the calculated color balance parameter to the buffer 382. Furthermore, the calculator 381 may also calculate a reciprocal of DB/DG as the color balance parameter.

The buffer 382 stores therein the color balance parameters which have been calculated by the calculator 381 and correspond to set frames. In the first embodiment, the buffer 382 stores therein the color balance parameters, which are associated with the in-vivo images, corresponding to several frames. If a new color balance parameter is input, the buffer 382 overwrites the oldest color balance parameter among the currently stored color balance parameters with the new color balance parameter, whereby the buffer 382 stores the color balance parameters by sequentially updating the same number of color balance parameters as the number of several frames in the order of the latest calculation time.

The fixed value memory 383 stores therein the color balance parameters that are previously set. In the first embodiment, the fixed value memory 383 stores therein the color balance parameters that are previously set such that the color balance suitable for the NBI observation is obtained. A description will be given with the assumption that absorption of blue light due to urine is not considered for the color balance parameters; however, the color balance parameters may also be set by considering the absorption of blue light due to urine.

The first selecting unit 384 selects, under the control of the mode setting unit 386, either the latest color balance parameter from the color balance parameters stored in the buffer 382 or the color balance parameter stored in the fixed value memory 383 and then outputs the selected color balance parameter to the first color balance processing unit 33. The latest color balance parameter mentioned here is the color balance parameter of the latest frame. Furthermore, if the input unit 37 receives an input of the freeze instruction signal, the first selecting unit 384 acquires the color balance parameter associated with the in-vivo image of the freeze target from the buffer 382 and outputs the acquired parameter to the first color balance processing unit 33. Even if the color balance parameter stored in the buffer 382 has been updated in the still image display period due to the operation of the freeze process, the first selecting unit 384 does not output the updated color balance parameter to the first color balance processing unit 33.

If the color balance parameter, specifically, DB/DG associated with the process signal input from the freeze processing unit 32, is input from the first selecting unit 384, the first color balance processing unit 33 multiplies the reciprocal of DB/DG by the B component signal of this process signal and then adjusts the signal value of the B component.

The second selecting unit 385 selects, under the control of the mode setting unit 386, in accordance with the set mode, either the latest color balance parameter stored in the buffer 382 or the color balance parameter stored in the fixed value memory 383 and inputs the selected color balance parameter to the second color balance processing unit 34.

If the input unit 37 receives an input of a mode setting instruction signal that indicates the setting of or the change in the observation mode, the mode setting unit 386 outputs, to the first selecting unit 384 and the second selecting unit 385, a selection instruction signal of the color balance parameter associated with the mode setting indication signal. Two modes are used for the observation mode: a normal observation mode in which a color balance process is performed by using color balance parameter that is stored in the fixed value memory 383 and that is previously set; and a correction observation mode in which color balance correction is performed for each in-vivo image by using the color balance parameter calculated by the calculator 381.

In the control unit 38, as described above, based on the selection instruction signal input from the mode setting unit 386, the first selecting unit 384 selects the color balance parameter and outputs the selected parameter to the first color balance processing unit 33, whereas the second selecting unit 385 selects the color balance parameter and outputs the selected parameter to the second color balance processing unit 34. Furthermore, if the input unit 37 receives an input of the freeze instruction signal, the control unit 38 allows the first selecting unit 384 to select the color balance parameter associated with the freeze target image that has been determined by the freeze processing unit 32 and allows the selected color balance parameter to be input to the first color balance processing unit 33. At this time, the first selecting unit 384 selects the color balance parameter of the frame associated with the freeze target image determined by the freeze processing unit 32. In the still image display period due to the operation of the freeze process in the correction observation mode, the second selecting unit 385 outputs, to the second color balance processing unit 34, the latest color balance parameters that are sequentially input to the buffer 382.

The storage unit 39 stores therein various programs for operating the endoscope system 1, and data including various parameters needed to operate the endoscope system 1, and the like. Furthermore, the storage unit 39 stores therein identification information on the processing device 3. Here, the identification information includes specific information (ID) on the processing device 3, the model year and specification information about the processing device 3, and the like.

Furthermore, the storage unit 39 stores therein various programs including an image acquisition processing program for executing image acquisition processing method performed by the processing device 3. It is possible to make various programs widely available by recording them in a computer readable recording medium, such as a hard disk, a flash memory, a CD-ROM, a DVD-ROM, or a flexible disk. Furthermore, the various programs described above can be acquired by downloading via a communication network. The communication network mentioned here is implemented by, for example, an existing public circuit, a local area network (LAN), a wide area network (WAN), or the like, irrespective of a wired or wireless network.

The storage unit 39 having the configuration described above is implemented by using a read only memory (ROM) that stores therein various programs or the like; a random access memory (RAM) that stores therein arithmetic parameters, data, or the like used for each process; a hard disk; and the like.

In the following, the configuration of the light source unit 3a will be described. The light source unit 3a includes an illumination unit 301 and an illumination controller 302. The illumination unit 301 emits, under the control of the illumination controller 302, illumination light with different amount of exposure toward the object (subject) by sequentially changing the illumination light. The illumination unit 301 includes a light source 301a and a light source driver 301b.

The light source 301a is formed by using a light source that emits white light or narrow-band light, one or a plurality of lenses, and the like and emits light (illumination light) when instructed. The illumination light produced by the light source 301a is emitted toward the object from the distal end of the distal end portion 24 via the light guide 241. In the first embodiment, because NBI observation suitable for observation in the urinary bladder is performed, the light source 301a can emit, as the illumination light, narrow-band light formed of narrow-band blue light (for example, 390 nm to 445 nm) and narrow-band green light (for example, 530 nm to 550 nm). Furthermore, for the light source 301a, one of the light sources from among an LED light source, a laser light source, a xenon lamp, a halogen lamp, and the like is used. Furthermore, the light source 301a may also be formed by using a filter that passes light with a predetermined wavelength band (in this case, a narrow-band).

The light source driver 301b supplies, under the control of the illumination controller 302, an electrical current to the light source 301a, thereby to cause the light source 301a to emit the illumination light.

Based on the control signal (light control signal) received from the control unit 38, the illumination controller 302 controls the amount of the electrical power to be supplied to the light source 301a and controls the timing of the light source 301a to be driven.

The display device 4 displays a display image associated with the image signal that has been received from the processing device 3 (the display image generating unit 36) via a video image cable. The display device 4 is formed by using a monitor, such as a liquid crystal or organic electro luminescence (EL) monitor.

Figure 4:
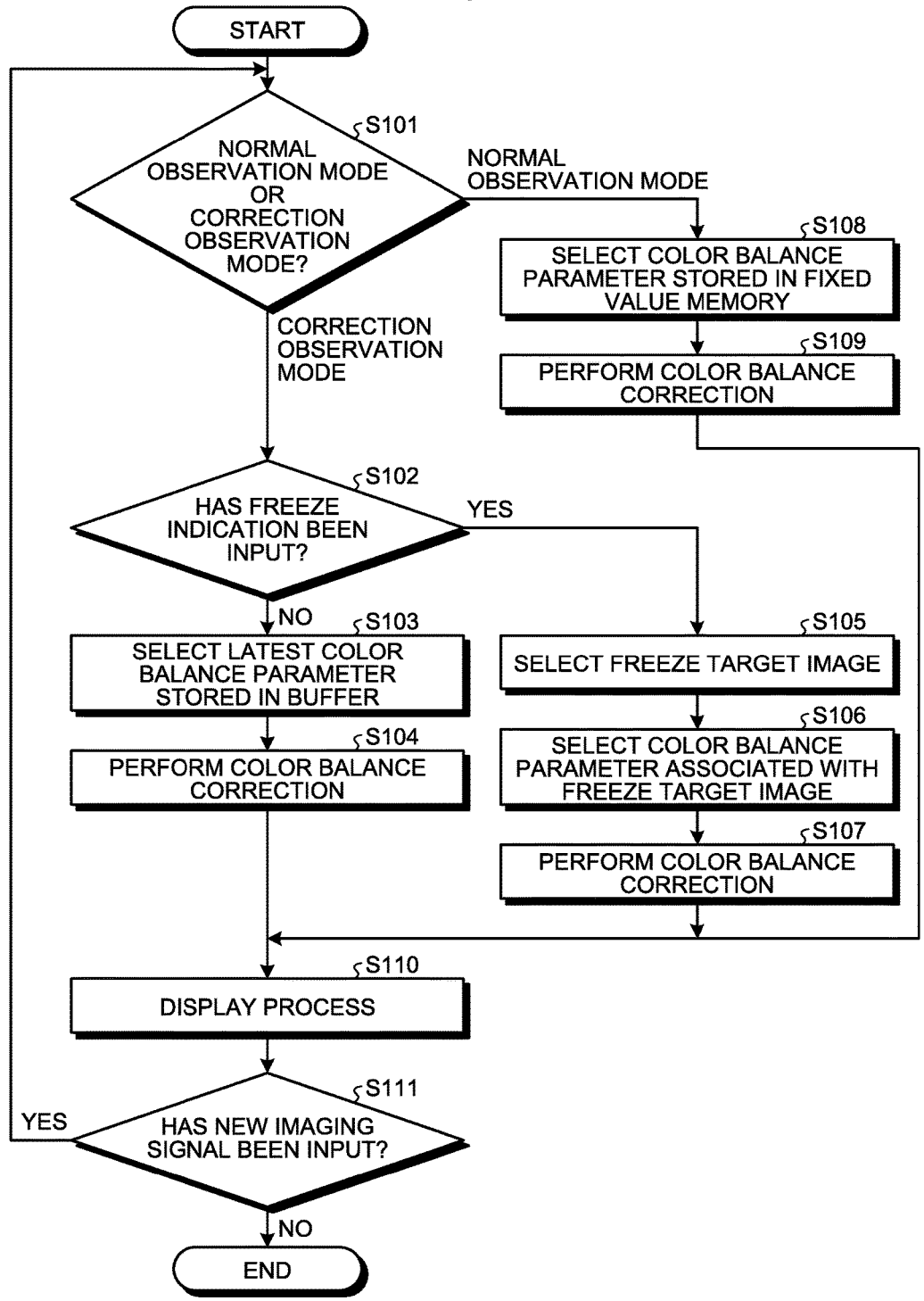
FIG. 4 is a flowchart illustrating image processing performed by the endoscope system according to the first embodiment of the present disclosure.

In the following, the image processing performed by the endoscope system 1 will be described. FIG. 4 is a flowchart illustrating image processing performed by the endoscope system according to the first embodiment of the present disclosure. In the following, a description will be given with the assumption that each of the units is operated under the control of the control unit 38. Furthermore, the description below is described about the process at the time of NBI observation; however, movement of the distal end portion 24 to the position in which NBI observation is performed is observed under, for example, white light.

If the imaging signal acquiring unit 31 acquires an imaging signal from the endoscope 2, the control unit 38 determines which observation mode is set, i.e., the normal observation mode or the correction observation mode (Step S101). If the control unit 38 determines that the normal observation mode is set to the observation mode (Step S101: normal observation mode), the image processing proceeds to Step S108. In contrast, if the control unit 38 determines that the correction observation mode is set to the observation mode (Step S101: correction observation mode), the image processing 38 proceeds to Step S102. Furthermore, the process signals are sequentially input to the second color balance processing unit 34 from the imaging signal acquiring unit 31, and the second color balance processing unit 34 performs color balance correction on the process signals based on the color balance parameters that are input from the second selecting unit 385. Then, a detection value associated with the process signal generated by the second color balance processing unit 34 is calculated by the detecting unit 35.

At Step S102, the control unit 38 determines whether the freeze instruction has been input via the input unit 37. If the control unit 38 determines that the freeze instruction has not been input (Step S102: No), the image processing proceeds to Step S103.

At Step S103, the first selecting unit 384 refers to, under the control of the mode setting unit 386, the buffer 382; selects the latest color balance parameter; and outputs the selected color balance parameter to the first color balance processing unit 33. Furthermore, the second selecting unit 385 refers to, under the control of the mode setting unit 386, the buffer 382; selects the latest color balance parameter; and outputs the selected color balance parameter to the second color balance processing unit 34. Furthermore, based on the latest input color balance parameter, the second color balance processing unit 34 performs color balance correction on the process signal.

At Step S104 subsequent to Step S103, the first color balance processing unit 33 performs, based on the color balance parameter input from the first selecting unit 384, color balance correction on the process signal that is input via the freeze processing unit 32. The first color balance processing unit 33 outputs the image signal that has been subjected to the color balance correction to the display image generating unit 36. Then, the image processing proceeds to Step S110.

In contrast, at Step S102, if the control unit 38 determines that the freeze instruction has been input (Step S102: Yes), the image processing proceeds to Step S105.

At Step S105, the freeze processing unit 32 refers to the time at which an input of the freeze instruction signal was received and then selects an in-vivo image as the freeze target. Then, the first selecting unit 384 refers to the buffer 382; selects the color balance parameter associated with the in-vivo image that has been selected as the freeze target; and outputs the selected color balance parameter to the first color balance processing unit 33 (Step S106).

Then, the first color balance processing unit 33 performs color balance correction on the process signal associated with the in-vivo image that has been selected as the freeze target based on the color balance parameter input from the first selecting unit 384 (Step S107). The first color balance processing unit 33 outputs the image signal that has been subjected to the color balance correction to the display image generating unit 36. Then, the image processing proceeds to Step S110.

Furthermore, at Step S108, the first selecting unit 384 refers to, under the control of the mode setting unit 386, the fixed value memory 383; selects the previously set color balance parameter; and outputs the selected color balance parameter to the first color balance processing unit 33. Furthermore, the second selecting unit 385 refers to, under the control of the mode setting unit 386, the fixed value memory 383; selects the previously set color balance parameter; and outputs the selected color balance parameter to the second color balance processing unit 34.

Then, the first color balance processing unit 33 performs color balance correction on the process signal input via the freeze processing unit 32 based on the color balance parameter that was input from the first selecting unit 384 (Step S109). The first color balance processing unit 33 outputs the image signal that has been subjected to the color balance correction to the display image generating unit 36. Then, the image processing proceeds to Step S110.

At Step S110, the display image generating unit 36 performs signal processing on the image signal generated by the first color balance processing unit 33 such that the image signals become signals displayable on the display device 4, and then generates a display purpose image signal. The display image generating unit 36 sends the generated display purpose image signal to the display device 4 and allows the display device 4 to display the image associated with the display purpose image signal. Incidentally, the image selected as the freeze target is displayed for a period of time longer than that of the other images.

After the display image generating unit 36 generates the image signal and controls the display, the control unit 38 determines whether a new image signal has been input (Step S111). If the control unit 38 determines that, for example, a new imaging signal has been input (Step S111: Yes), the image processing returns to Step S101 and repeats the process described above, whereas, if the control unit 38 determines that a new imaging signal has not been input (Step S111: No), the image processing is terminated.

In the image processing described above, every time a process signal is input to the imaging signal acquiring unit 31, a detection value is calculated by the second color balance processing unit 34 and the detecting unit 35 and, furthermore, the calculator 381 calculates a color balance parameter based on the detection value. Consequently, even if, after having displayed an image of the freeze target as a still image display, the freeze image display again returns to the moving image display, it is possible to display the moving image with an appropriate color balance parameter.

According to the first embodiment described above, the first color balance processing unit 33 performs the color balance correction on the process signal associated with the in-vivo image as the display target and, in parallel with this process, the process of color balance correction is performed by the second color balance processing unit 34 and the calculation of the color balance parameter is performed the calculator 381. Consequently, because a color balance parameter is generated every time the imaging signal is input, if correction is performed on the image to be displayed in real time, it is possible to generate an image having the color balance suitable for observation even after the freeze process of the image has been released.

According to the first embodiment described above, because the second color balance processing unit 34 acquires the latest color balance parameters from the second selecting unit 385 and performs the color balance correction, it is possible to maintain the accuracy of the detection result obtained by the detecting unit 35.

Second Embodiment

Figure 5:
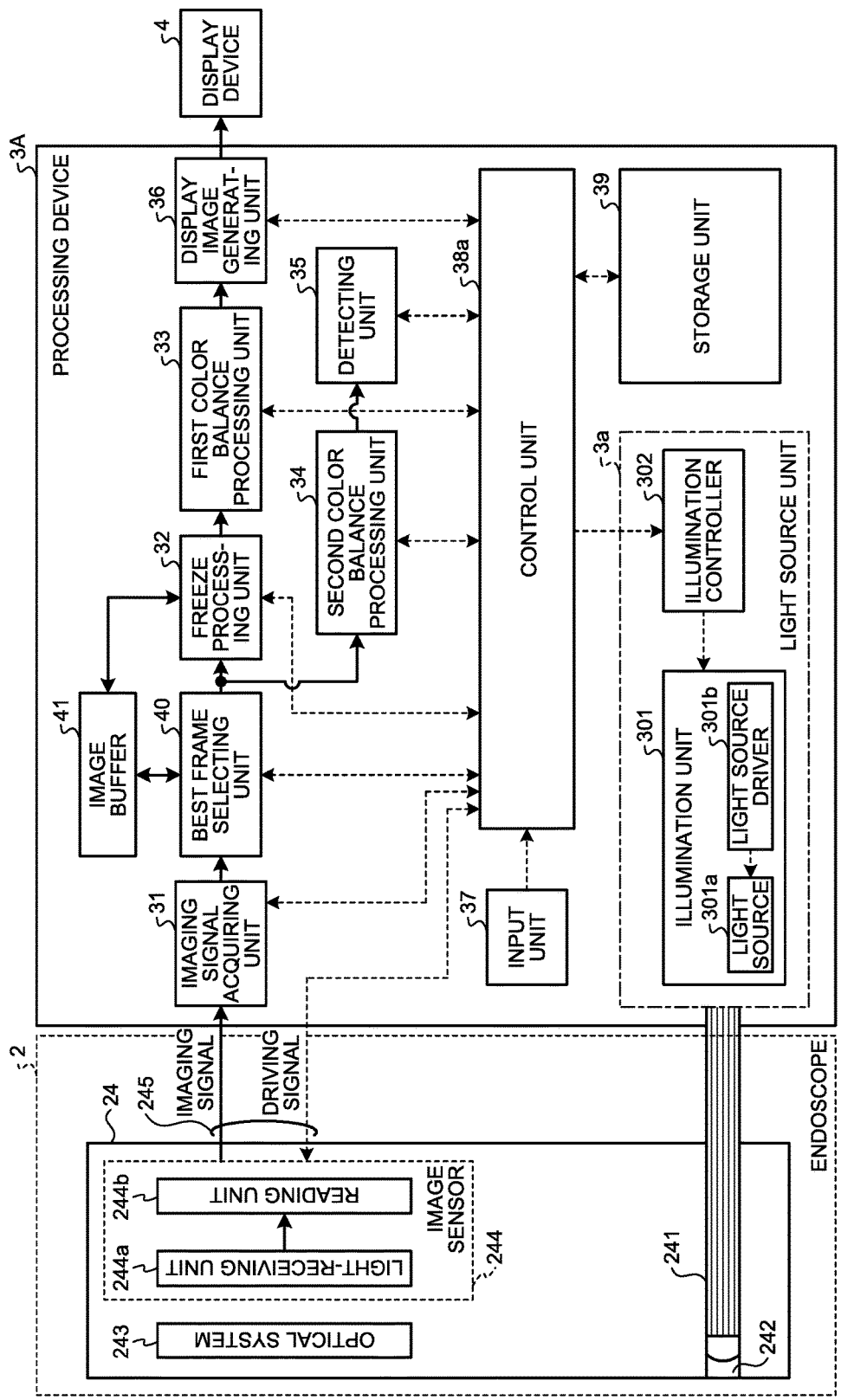
FIG. 5 is a diagram schematically illustrating an endoscope system according to a second embodiment of the present disclosure.

In the following, a second embodiment according to the present disclosure will be described. In the first embodiment described above, a description has been given with the assumption that the image obtained at the timing in which an input of the freeze instruction is received as the image of the display target; however, an endoscope system according to the second embodiment has a pre freeze function of selecting, as an image of the display target, an image with small blurring acquired in a predetermined period of time extending back from a timing in which an input of the freeze instruction is received. Furthermore, regarding the configuration of the endoscope system according to the second embodiment of the present disclosure, components having the same configuration as that of the endoscope system 1 described above are assigned the same reference numerals. FIG. 5 is an outlined block diagram of an endoscope system according to a second embodiment of the present disclosure.

An endoscope system 1A illustrated in FIG. 5 includes the endoscope 2 and the display device 4, which are described above, and includes a processing device 3A that performs overall control of the operation of the endoscope system 1A and that includes the light source unit 3a that produces illumination light emitted from the distal end of the endoscope 2 and that performs predetermined signal processing on the imaging signals captured by the endoscope 2.

The processing device 3A includes the imaging signal acquiring unit 31, the freeze processing unit 32, the first color balance processing unit 33, the second color balance processing unit 34, the detecting unit 35, the display image generating unit 36, the input unit 37, a control unit 38a, the storage unit 39, a best frame selecting unit 40, and an image buffer 41. Namely, the processing device 3A according to the second embodiment further includes, in addition to the components included in the endoscope system 1 described above, the control unit 38a instead of the control unit 38, the best frame selecting unit 40, and the image buffer 41.

The best frame selecting unit 40 inputs a process signal from the imaging signal acquiring unit 31 and outputs the process signal to the image buffer 41 and the freeze processing unit 32. The best frame selecting unit 40 is an image selecting unit that selects, in accordance with an input of the freeze instruction signal, the in-vivo image with small blurring as the image of the best frame from the in-vivo images stored in the image buffer 41. The best frame selecting unit 40 outputs a best frame selection signal that includes the information about the selected frame to the freeze processing unit 32 and the control unit 38a. When the freeze instruction signal is input, the best frame selecting unit 40 may also calculate blurring of the plurality of in-vivo images stored in the image buffer 41 and select the in-vivo image of the best frame based on the calculated blurring. Alternatively, every time an imaging signal is input from the imaging signal acquiring unit 31, the best frame selecting unit 40 may also calculate blurring of the in-vivo image associated with the input imaging signal and then stores the in-vivo image in the image buffer 41 by associating the calculated blurring with the in-vivo image. The blurring of the in-vivo image is calculated by using a known calculation method.

The freeze processing unit 32 acquires the process signal associated with the in-vivo image having the frame number of the frame selected by the best frame selecting unit 40 and sets the acquired in-vivo image to the in-vivo image of the freeze target. The freeze processing unit 32 outputs the process signal of the acquired in-vivo image of the freeze target to the first color balance processing unit 33.

The image buffer 41 stores therein the same number of process signals, which are input via the best frame selecting unit 40, as the number of set frames. The image buffer 41 stores a quantity of process signals input via the best frame selecting unit 40, the quantity corresponding to a predetermined number of frames. In the second embodiment, the image buffer 41 stores therein a quantity of process signals corresponding to several frames. If a new process signal is input, by overwriting the oldest process signal among the currently stored process signals with this new process signal, the image buffer 41 stores therein the in-vivo images by sequentially updating the quantity of in-vivo images corresponding to the set several frames in the order of the latest acquisition time.

FIG. 6 is a block diagram of a relevant part of the endoscope system according to the second embodiment of the present disclosure, specifically, a block diagram of the control unit 38a. The control unit 38a includes the calculator 381, the fixed value memory 383, the first selecting unit 384, the second selecting unit 385, the mode setting unit 386, a first buffer 387, and a second buffer 388. In the second embodiment, both the first buffer 387 and the second buffer 388 forms a correction purpose buffer.

The first buffer 387 stores the color balance parameters which have been calculated by the calculator 381 and corresponds to set frames. In the second embodiment, the first buffer 387 stores therein the color balance parameters associated with the plurality of process signals (in-vivo images) stored in the image buffer 41. If a new color balance parameter is input, the first buffer 387 overwrites the oldest color balance parameter among the currently stored color balance parameters with the new color balance parameter, whereby the first buffer 387 stores the color balance parameters by sequentially updating the same number of color balance parameters as the number of several frames in the order of the latest calculation time.

Furthermore, if the best frame selection signal including the information on the frame selected by the best frame selecting unit 40 is input, the first buffer 387 inputs, under the control of the control unit 38a, the color balance parameter associated with the corresponding frame to the second buffer 388. If the best frame selection signal is not input, the first buffer 387 inputs the latest color balance parameter to the second buffer 388.

The second buffer 388 stores therein the color balance parameter input from the first buffer 387. If a new color balance parameter is input from the first buffer 387, the second buffer 388 overwrites the input color balance parameter with the currently stored color balance parameter, whereby the second buffer 388 sequentially updating the color balance parameters.

The first selecting unit 384 selects, under the control of the mode setting unit 386, either the color balance parameter stored in the second buffer 388 or the color balance parameter stored in the fixed value memory 383 and then outputs the selected color balance parameter to the first color balance processing unit 33. Furthermore, if the input unit 37 receives an input of the freeze instruction signal, the first selecting unit 384 acquires the color balance parameter associated with the in-vivo image of the freeze target from the second buffer 388 and outputs the color balance parameter to the first color balance processing unit 33.

The second selecting unit 385 selects, under the control of the mode setting unit 386, either the color balance parameter stored in the second buffer 388 or the color balance parameter stored in the fixed value memory 383 and then outputs the selected color balance parameter to the second color balance processing unit 34.

In the control unit 38a, based on the selection instruction signal that is input from the mode setting unit 386, the first selecting unit 384 selects a color balance parameter and outputs the selected parameter to the first color balance processing unit 33, whereas the second selecting unit 385 selects a color balance parameter and outputs the selected parameter to the second color balance processing unit 34. Furthermore, if a best frame selection signal is input from the best frame selecting unit 40, the control unit 38a allows the first buffer 387 to select the color balance parameter associated with the best frame selection signal and allows the selected color balance parameter to be input to the second buffer 388. The first selecting unit 384 acquires the color balance parameter associated with the in-vivo image of the best frame from the second buffer 388 and outputs the acquired parameter to the first color balance processing unit 33.

In the following, image processing performed by the endoscope system 1A will be described. FIG. 7 is a flowchart illustrating image processing performed by the endoscope system according to the second embodiment of the present disclosure. In a description below, a description will be given with the assumption that each of the units is operated under the control of the control unit 38a.

If the imaging signal acquiring unit 31 acquires an imaging signal from the endoscope 2, the control unit 38a determines which observation mode is set, i.e., the normal observation mode or the correction observation mode (Step S201). If the control unit 38a determines that the normal observation mode is set to the observation mode (Step S201: normal observation mode), the image processing proceeds to Step S208. In contrast, if the control unit 38a determines that the correction observation mode is set to the observation mode (Step S201: correction observation mode), the image processing proceeds to Step S202. Furthermore, the process signals acquired by the imaging signal acquiring unit 31 are sequentially input to the second color balance processing unit 34 and the second color balance processing unit 34 performs color balance correction on the process signals based on the color balance parameters input from the second selecting unit 385. Then, a detection value associated with the image signal generated by the second color balance processing unit 34 is calculated by the detecting unit 35.

At Step S202, the control unit 38a determines whether the freeze instruction has been input via the input unit 37. If the control unit 38a determines that the freeze instruction has not been input (Step S202: No), the image processing proceeds to Step S203.

At Step S203, the first selecting unit 384 refers to, under the control of the mode setting unit 386, the second buffer 388; selects the latest color balance parameter; and outputs the selected color balance parameter to the first color balance processing unit 33. Furthermore, the second selecting unit 385 refers to, under the control of the mode setting unit 386, the second buffer 388; selects the latest color balance parameter; and outputs the selected color balance parameter to the second color balance processing unit 34. Furthermore, based on the latest input color balance parameter, the second color balance processing unit 34 performs color balance correction on the process signal.

At Step S204 subsequent to Step S203, the first color balance processing unit 33 performs, based on the color balance parameter input from the first selecting unit 384, color balance correction on the process signal input via the freeze processing unit 32. The first color balance processing unit 33 outputs the image signal that has been subjected to the color balance correction to the display image generating unit 36. Then, the image processing to Step S210.

In contrast, at Step S202, if the control unit 38a determines that the freeze instruction has been input (Step S202: Yes), the image processing proceeds to Step S205.

At Step S205, based on the blurring stored in the image buffer 41, the best frame selecting unit 40 selects the in-vivo image as the freeze target. The best frame selecting unit 40 outputs the best frame selection signal including the information on the selected frame to the control unit 38a. Consequently, the color balance parameter associated with the in-vivo image of the best frame is input from the first buffer 387 to the second buffer 388. Then, the first selecting unit 384 refers to the second buffer 388; selects color balance parameter associated with the in-vivo image that was selected as the best frame for the freeze target and then outputs the selected color balance parameter to the first color balance processing unit 33 (Step S206).

Then, the first color balance processing unit 33 performs the color balance correction on the process signal associated with the in-vivo image selected as the freeze target based on the color balance parameter input from the first selecting unit 384 (Step S207). The first color balance processing unit 33 outputs the image signal that has been subjected to the color balance correction to the display image generating unit 36. Then, the image processing proceeds to Step S210.

Furthermore, at Step S208, the first selecting unit 384 refers to, under the control of the mode setting unit 386, the fixed value memory 383; selects the previously set color balance parameter; and outputs the selected color balance parameter to the first color balance processing unit 33. Furthermore, the second selecting unit 385 refers to, under the control of the mode setting unit 386, the fixed value memory 383; selects the previously set color balance parameter; and outputs the selected color balance parameter to the second color balance processing unit 34.

Then, based on the color balance parameter input from the first selecting unit 384, the first color balance processing unit 33 performs the color balance correction on the process signal input via the freeze processing unit 32 (Step S209). The first color balance processing unit 33 outputs the image signal that has been subjected to the color balance correction to the display image generating unit 36. Then, the image processing proceeds to Step S210.

At Step S210, the display image generating unit 36 performs the signal processing on the image signal generated by the first color balance processing unit 33 such that the image signals become signals displayable on the display device 4, and then generates a display purpose image signal. The display image generating unit 36 sends the generated display purpose image signal to the display device 4 and allows the display device 4 to display the image associated with the subject display purpose image signal. Incidentally, the image selected as the freeze target is displayed for a period of time longer than that of the other images.

After the display image generating unit 36 generates the image signal and controls the display, the control unit 38a determines whether a new imaging signal has been input (Step S211). If the control unit 38a determines that, for example, a new imaging signal has been input (Step S211: Yes), the image processing returns to Step S201 and repeats the process described above, whereas, if the control unit 38a determines that a new imaging signal has not been input (Step S211: No), the image processing is terminated.

In the image processing described above, every time the process signal is input from the imaging signal acquiring unit 31, a detection value is calculated by the second color balance processing unit 34 and the detecting unit 35 and, furthermore, the calculator 381 calculates a color balance parameter based on the detection value. Consequently, even if, after having displayed an image of the freeze target as a still image display, the freeze image display again returns to the moving image display, it is possible to display the moving image with an appropriate color balance parameter.

According to the second embodiment described above, the first color balance processing unit 33 performs the color balance correction on the process signal associated with the in-vivo image as the display target and, in parallel with this process, the process of the color balance correction is performed by the second color balance processing unit 34 and the calculation of the color balance parameter is performed by the calculator 381. Consequently, when correction is performed, in real time, on the image to be displayed, it is possible to generate an image having the color balance suitable for observation even after the freeze has been released.

Furthermore, according to the second embodiment described above, if a freeze instruction signal is input, the best frame selecting unit 40 selects the in-vivo image with small blurring from the plurality of in-vivo images stored in the image buffer 41; therefore, it is possible to set the in-vivo image that is to be displayed as the freeze image to the in-vivo image suitable for observation. Consequently, the in-vivo image can be more easily viewed, which makes it possible to perform more accurate diagnosis.

Furthermore, according to the second embodiment described above, because the correction purpose buffer formed of the first buffer 387 and the second buffer 388 stores only the color balance parameters, the storage capacity of the buffers can be reduced when compared with the case in which the color balance parameters are stored together with the in-vivo images.

Furthermore, in the first and the second embodiments described above, a description has been given of a case in which the imaging signal acquiring unit 31 generates the process signals including the images to which each of the RGB color components is added; however, the imaging signal acquiring unit 31 may also generate process signals having the YCbCr color space including the luminance (Y) components and the color difference components based on the YCbCr color space or may also generate process signals having components by separating the components into colors and luminance by using the HSV color space formed of three components of hue (Hue), saturation (saturation chroma), and value (value lightness brightness) or L*a*b*color space that uses a three dimensional space.

Furthermore, in the first and the second embodiments described above, a description has been given of a case in which either the normal observation mode or the correction observation mode is set to the observation mode by the mode setting unit 386; however, as the configuration without providing the mode setting unit 386, only the correction observation mode may also be operated.

Furthermore, in the first and the second embodiments described above, a description has been given of a case in which the calculator 381, the buffer 382, the fixed value memory 383, the first selecting unit 384, the second selecting unit 385, the mode setting unit 386, the first buffer 387, the second buffer 388 are provided in each of the control units 38 and 38a; however, the control units 38 and 38a may also be individually provided.

Furthermore, in the first and the second embodiments described above, a description has been given of a case of using the simultaneous illumination/imaging method in which narrow-band light is emitted from the light source unit 3a and the light-receiving unit 244a receives the reflected light of illumination light; however, it may also be possible to use a frame sequential illumination/imaging method in which the light source unit 3a individually and sequentially emits each pieces of narrow-band light having different color components and the light-receiving unit 244a receives the pieces of light having the different color components.

Furthermore, in the first and the second embodiments described above, a description has been given of a case in which the light source unit 3a is formed by being separated from the endoscope 2; however, for example, it may also be possible to use the configuration in which a light source device is provided in the endoscope 2, such as a semiconductor light source being provided at the distal end of the endoscope 2. Furthermore, the function of the processing device 3 may also be added to the endoscope 2.

Furthermore, in the first and the second embodiments described above, a description has been given of a case in which the light source unit 3a and the processing device 3 are integrally formed; however, it may also be possible to use the configuration in which the light source unit 3a and the processing device 3 are separately formed and, for example, the illumination unit 301 and the illumination controller 302 are provided outside the processing device 3. Furthermore, the light source 301a may also be provided at the distal end of the distal end portion 24.

Furthermore, in the first and the second embodiments described above, a description has been given of a case of performing NBI observation that uses narrow-band light formed of narrow-band blue light (for example, 390 nm to 445 nm) and narrow-band green light (for example, 530 nm to 550 nm); however, the range of the wavelength band and the combination of narrow-bands are not limited. For example, it may also be possible to use light including narrow-band red light or narrow-band infrared light or use white light.

Furthermore, in the first and the second embodiments described above, a description has been given of a case in which the endoscope system according to the present disclosure is the endoscope system 1 that uses the flexible endoscope 2 used for biological tissues inside the subject that is the observation target; however, it may also be possible to use an endoscope system using a rigid endoscope, an industrial endoscope that observes the characteristics of materials, a capsule endoscope, a fiberscope, and an endoscope in which a camera head is connected to an eyepiece portion of an optical endoscope, such as an optical sight tube.

Furthermore, in the first and the second embodiments described above, the endoscope system has been described as an example; however, it may also be possible to use a case in which, for example, video images are output to an electronic view finder (EVF) provided in a digital still camera or the like.

According to the present disclosure, even if correction is performed in real time, an advantage is provided in that it is possible to generate color balance images suitable for observation after releasing freeze.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
a processor comprising hardware, wherein the processor is configured to:
acquire, in time series, an imaging signal generated by capturing an object;
determine, when a freeze instruction signal that allows an image based on the imaging signal to be displayed as a still image is input, an image of a freeze target, thereby to specify an imaging signal corresponding to the image of the freeze target, or determine, when the freeze instruction signal is not input, a latest image as an image to be displayed, thereby to specify an imaging signal corresponding to the image to be displayed;
perform a color balance adjustment process by using a first color balance parameter, based on the imaging signal corresponding to the image which is determined to be either one of the image of the freeze target and the latest image in the determining, thereby to generate a first imaging signal;
generate a display purpose imaging signal, based on the generated first imaging signal;
perform the color balance adjustment process by using a second color balance parameter, based on the imaging signal corresponding to the image which is determined to be either one of the image of the freeze target and the latest image in the determining, in parallel with the performing the color balance adjustment process by using the first color balance parameter, thereby to generate a second imaging signal;
detect signals of a plurality of color components that are included in the second imaging signal;
calculate, based on the detected signals, a color balance parameter used for performing the color balance adjustment process; and
set, when the freeze instruction signal is not input, a latest color balance parameter that has been calculated in the calculating as the first and the second color balance parameters, or set, when the freeze instruction signal is input, a color balance parameter corresponding to the image of the freeze target as the first color balance parameter and the latest color balance parameter as the second color balance parameter.

2. The image processing apparatus according to claim 1, further comprising:
an image buffer that stores therein a plurality of the imaging signals acquired the acquiring by sequentially updating the imaging signals; and
a correction purpose buffer that stores therein color balance parameters associated with the imaging signals stored in the image buffer by sequentially updating the color balance parameters, wherein
the processor is further configured to:
select, when the freeze instruction signal is input, an image with small blurring from images associated with the plurality of imaging signals stored in the image buffer; and determine the image selected in the selecting as the image of the freeze target.

3. The image processing apparatus according to claim 2, further comprising a correction value memory that stores therein a previously set color balance parameter, wherein
the processor is further configured to:
set either one of a first mode in which the color balance adjustment process is performed by using the previously set color balance parameter and a second mode in which the color balance adjustment process is performed based on the color balance parameter calculated in the calculating; and
select, in accordance with the set mode, the color balance parameter that is to be set as the first color balance parameter.

4. The image processing apparatus according to claim 3, wherein
the correction purpose buffer stores the color balance parameter regardless of the set mode, and
the processor is further configured to set, when the first mode is set, the previously set color balance parameter as the first color balance parameter, set, when the second mode is set, the latest color balance parameter stored in the correction purpose buffer as the first color balance parameter, and set, when, the freeze instruction signal is input in the second mode, the color balance parameter associated with the image of the freeze target as the first color balance parameter.

5. The image processing apparatus according to claim 1, further comprising a input device that inputs the freeze instruction signal.

* * * * *